(12) United States Patent
Kim (10) Patent No.: US 7,785,006 B2
(45) Date of Patent: Aug. 31, 2010

(54) MEDICAL DIAGNOSTIC APPARATUS WITH LENGTH-ADJUSTABLE ARM STRUCTURE

(76) Inventor: Ik-Han Kim, 201-1103, Doosan Apt., Myeonmok 7 (chil)-dong, Jungnang-gu, Seoul, 131-755 (KR)

( * ) Notice: Subject to any disclaimer, the term of this patent is extended or adjusted under 35 U.S.C. 154(b) by 0 days.

(21) Appl. No.: 12/043,878

(22) Filed: Mar. 6, 2008

(65) Prior Publication Data

US 2009/0225956 A1 Sep. 10, 2009

(51) Int. Cl.
*H05G 1/02* (2006.01)
(52) U.S. Cl. .......................... 378/197; 378/181
(58) Field of Classification Search ............. 378/193, 378/197, 205, 181
See application file for complete search history.

(56) References Cited

U.S. PATENT DOCUMENTS 4,412,346 A * 10/1983 Takenouti et al. ........... 378/181

* cited by examiner

*Primary Examiner*—Jurie Yun
(74) *Attorney, Agent, or Firm*—John K. Park; Park Law Firm (57) ABSTRACT

A medical diagnostic apparatus using X-ray photography and having a length-adjustable arm structure is disclosed. The medical diagnostic apparatus according to the present invention comprises an X-ray generation unit, a first arm moving the X-ray generation unit forward and backward, a detector unit, a second arm connected to the detector unit, and a main body, a vertical drive motor and a rotational drive motor. The second arm comprises a guide rod connected to the main body; a drive motor rotating the guide rod; and a guide groove unit including a guide rod hole which is screw-fitting with the guide rod; a second guide plate disposed on both sides of the guide rod, and a guide rail formed on an inside of the second guide plate; a plurality of rollers to contact with the guide rail, and a guide rail groove to insert the guide rail therein.

2 Claims, 10 Drawing Sheets

MEDICAL DIAGNOSTIC APPARATUS WITH LENGTH-ADJUSTABLE ARM STRUCTURE

BACKGROUND OF THE INVENTION

1. Field of the Invention

The present invention relates to a medical diagnostic apparatus, and more particularly to a medical diagnostic apparatus using X-ray photography and having a length-adjustable arm structure.

2. Description of the Related Art

Generally, an X-ray diagnostic apparatus photographs an object using an X-ray to obtain an image of a diseased part of the object and diagnose the diseased part by reading the obtained image.

Figure 9A:
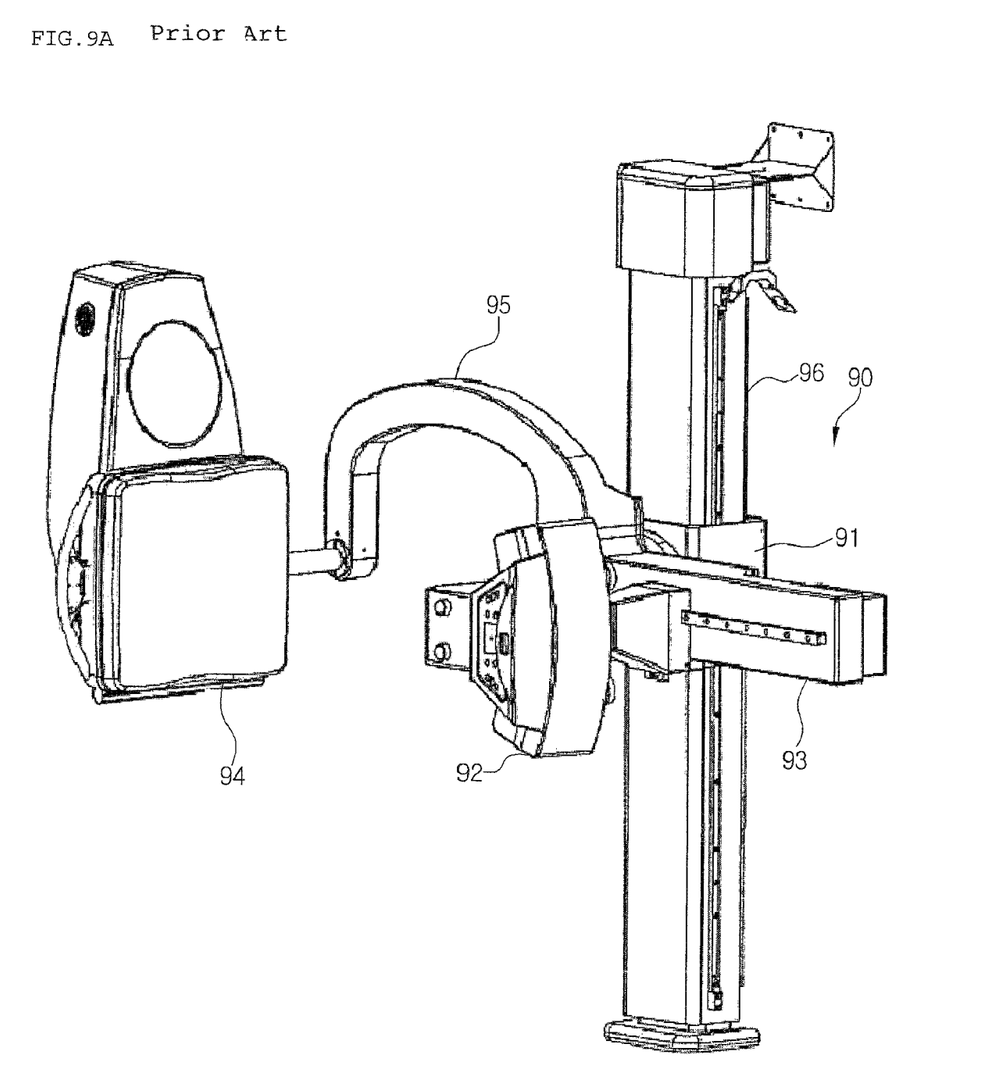
FIG. 9a is a perspective view and FIG. 9b is a front view.

A diagnostic apparatus 90 shown in FIG. 9 is suggested as an example of the X-ray diagnostic apparatuses. The diagnostic apparatus 90 comprises an elevator unit 91 mounted to a main body 96 to be movable up and down by a built-in elevation actuator, an X-ray generation unit 92 mounted to one side of the elevator unit 91 to be movable through an arm 93, and an X-ray detection unit 94 mounted to the other side of the elevator unit 91 through a C-shape arm 95.

The X-ray generation unit 92 and the X-ray detection unit 94 are facing each other with respect to the elevator unit 91. Since the arms 93 and 95 are rotatable with respect to the elevator unit 91, X-ray photographing can be performed with a patient not only in a standing position but also in a lying position on a table if the patient is hardly able to carry him/herself and keep standing during the X-raying. In this case, more specifically, the patient is laid on the table and the X-raying is performed as the table is passed through a curve of the C-shape arm 95. Thus, the X-ray images can be photographed at various angles without directly moving the diagnostic apparatus or the patient.

Meanwhile, in the X-ray diagnostic apparatus, a certain range of a source-to-image distance (SID), that is, a distance from an X-ray source to a detector unit needs to be secured. Generally, about 1000~1800 mm of the SID, more particularly, about 1800 mm when performing a horizontal photographing with the patient in a standing position to about 1000 mm when performing a vertical photographing with the patient in a lying position is required.

In the conventional diagnostic apparatus 90 as the above, a central axis of the main body is distanced to the C-shape arm 95 by about 1000 mm in order to secure the maximal SID for the horizontal photographing, and the C-shape arm 95 has at least an 800 mm length. On the other hand, while the maximal SID for the vertical photographing is 1000 mm, about a 1300 mm distance is required as a maximal elevating distance with a lowermost point of the elevator unit 91 guaranteed as well. Furthermore, the C-shape arm 95 of the conventional diagnostic apparatus 90 has a fixed length and is immovable.

Figure 9B:
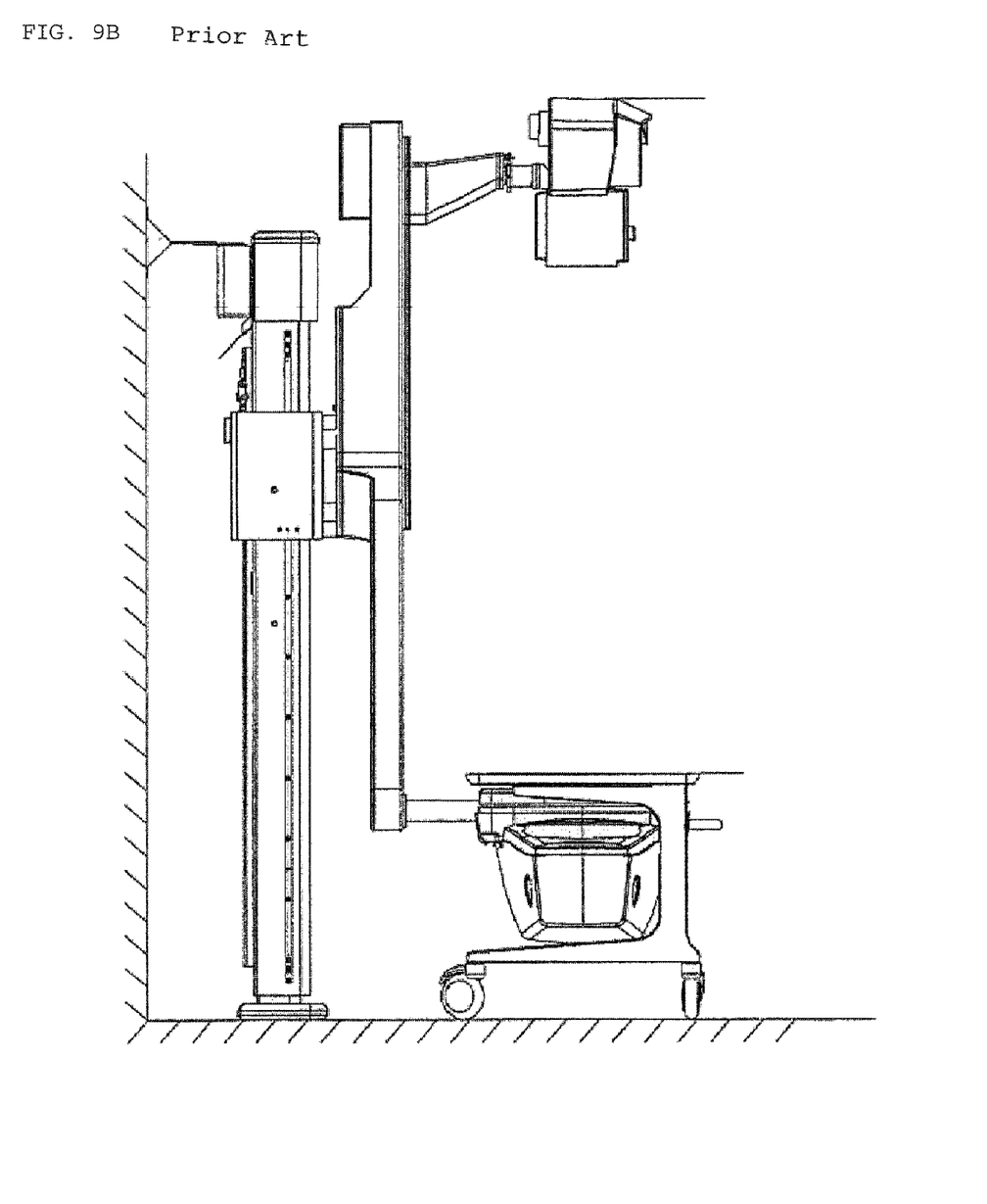

As shown in FIG. 9b, the conventional diagnostic apparatus 90 has at least a 2.2 m height at the main body. In a position for the vertical photographing, where the table is passed through with the patient laid thereon, a distance from a mounting floor of the diagnostic apparatus 90 to an end of the C-shape arm 95 is at least 2.5 m.

However, since a floor height of general buildings is not greater than 2.5 m, such a conventional diagnostic apparatus is difficult to be installed in general buildings. In addition, when the lengths of the main body and the arms 93 and 95 are controlled for use in general buildings, the maximal SID is hardly achieved in case of performing the horizontal photographing keeping the patient in the standing position.

Accordingly, a diagnostic apparatus capable of guaranteeing the maximal SID for the horizontal photographing and facilitating the installation in buildings with a general floor height has been in need.

SUMMARY OF THE INVENTION

Therefore, the present invention has been made in view of the above problems, and it is an object of the present invention to provide a medical diagnostic apparatus capable of being favorably installed in buildings with a general floor height while satisfying a maximal SID, by replacing a conventional C-shape arm with a U-shape arm which is length-adjustable.

It is another object of the present invention to provide a medical diagnostic apparatus capable of reducing a length of a main body while increasing a maximum movable distance of an elevator unit compared to in a conventional diagnostic apparatus, and also capable of reducing length of arms connected to the main body and an X-ray generation unit.

In accordance with the present invention, the above and other objects can be accomplished by the provision of a medical diagnostic apparatus comprising an X-ray generation unit, a first arm moving the X-ray generation unit forward and backward, a detector facing the X-ray generation unit and receiving an X-ray emitted from the X-ray generation unit, a second arm connected to the detector unit, and a main body including an elevator unit connected with one end of each the first arm and the second arm, a vertical drive motor moving the elevator unit, a rotation drive motor rotating the elevator unit, and an elevation rail mounted for the elevator unit to move vertically therealong, wherein the second arm comprises a guide rod connected to the main body, a drive motor rotating the guide rod, and a guide groove unit including a guide rod hole formed with a screw thread for screw-fitting with the guide rod to insert therein the guide rod.

The second arm may further comprise a second guide plate disposed on both sides of the guide rod, and a guide rail additionally formed on an inside of the second guide plate, and the guide groove unit further comprises a plurality of rollers formed on both sides thereof to contact with the guide rail, and a guide rail groove formed also on both sides thereof to insert the guide rail therein.

The second arm may further comprise a pair of limit switches respectively formed on upper and lower parts of one end of the second guide plate, and the guide groove unit further comprises a first stopper formed at an upper part of the one end of the guide rail groove and brought into contact with the upper limit switch of the pair of limit switches, and a second stopper formed at a lower part of the other end of the guide rail groove and brought into contact with the lower limit switch of the pair of limit switches.

BRIEF DESCRIPTION OF THE DRAWINGS

The above and other objects, features and other advantages of the present invention will be more clearly understood from the following detailed description taken in conjunction with the accompanying drawings, in which:

FIG. 9 is a view of a conventional medical diagnostic apparatus and more particularly.

DETAILED DESCRIPTION OF THE PREFERRED EMBODIMENTS

Hereinafter, an exemplary embodiment of the present invention will be described in detail with reference to the accompanying drawings.

Figure 1:
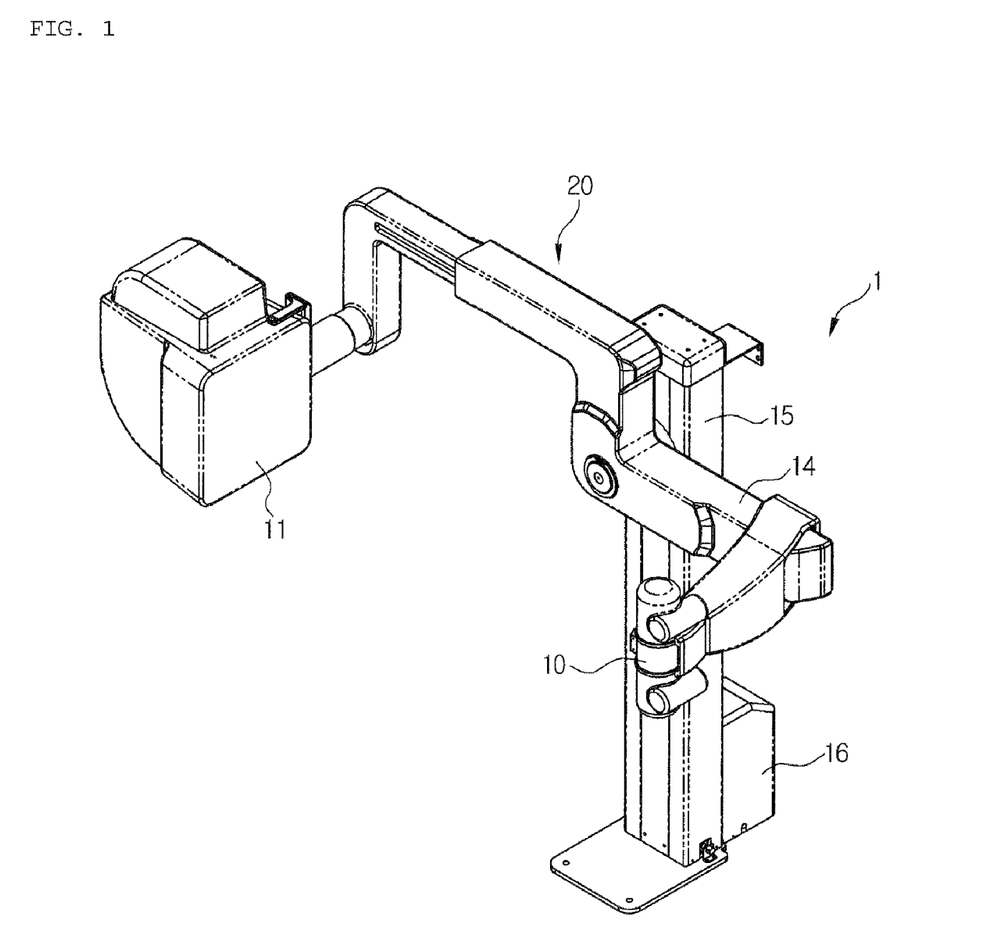
FIG. 1 is a perspective view of a medical diagnostic apparatus according to an embodiment of the present invention.
Figure 2:
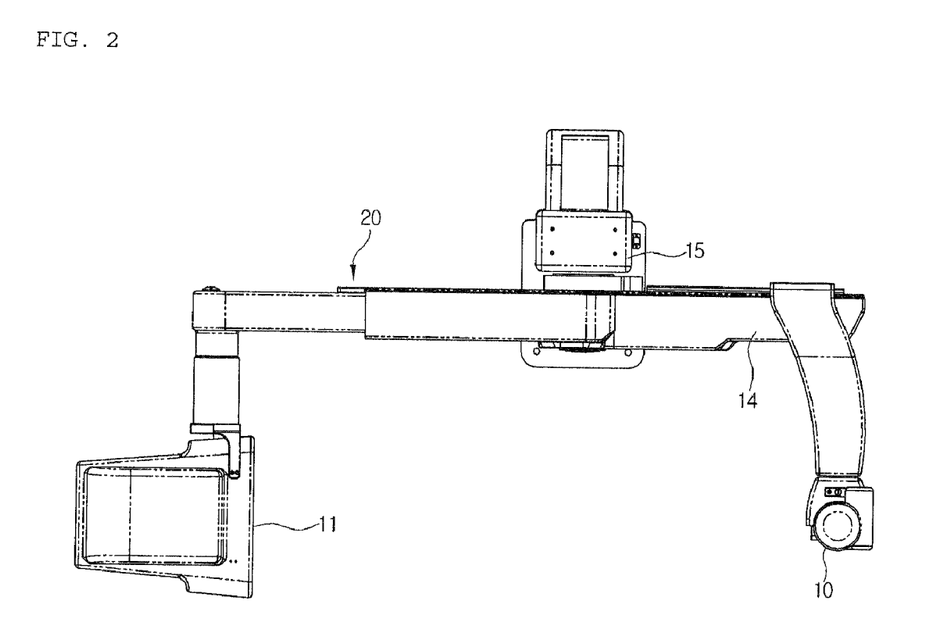
FIG. 2 is a plan view of the medical diagnostic apparatus according to the embodiment of the present invention.
Figure 3:
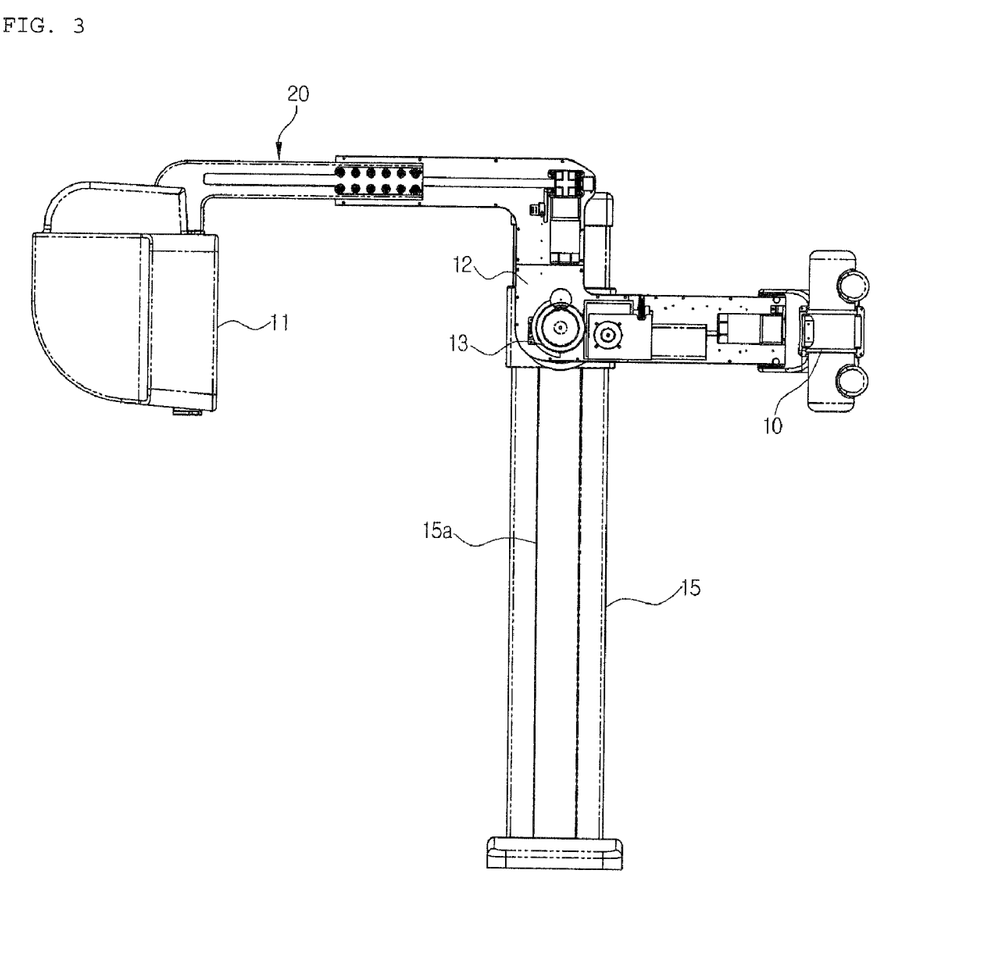
FIG. 3 is a front view of the medical diagnostic apparatus according to the embodiment of the present invention, with an arm cover detached.

FIG. 1 is a perspective view and FIG. 2 is a plan view both showing a medical diagnostic apparatus 1 according to an embodiment of the present invention. FIG. 3 shows the medical diagnostic apparatus according to the embodiment of the present invention with an arm cover detached.

Referring to FIG. 1 through to FIG. 3, the medical diagnostic apparatus 1 comprises an X-ray generation unit 10, a detection unit 11, a main body 15, a first arm 14, and a second arm 20.

Figure 8:
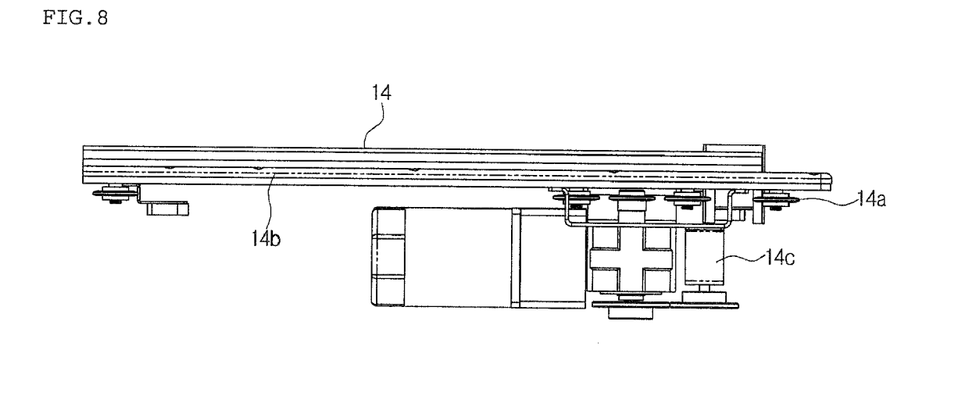
FIG. 8 is a view showing a first arm of the medical diagnostic apparatus according to the embodiment of the present invention.

The X-ray generation unit 10 is connected to the main body 15 through the first arm 14 and moved forward and backward by the first arm 14. In the first arm 14 comprising a plurality of sprockets 14a, a first guide plate 14b and a first drive motor 14c (refer to FIG. 8), as the sprockets 14a contacting with the first guide plate 14b are rotated by the first drive motor 14c, the sprockets 14a are chain-connected to the first guide plate 14b. According to this, the X-ray generation unit 10 in connection with the first arm 14 is moved forward and backward.

One end of the first arm 14 is connected with an elevator unit 12 mounted to the main body 15. The elevator unit 12 is moved up and down along an elevation rail 15a formed on the main body 15 by a vertical drive motor 16 mounted to the main body 15.

A rotation drive motor 13 not only drives the elevator unit 12 for the vertical movement, but also rotates the first arm 14 connected to the elevator unit 12 and the second arm 20 which will be explained later. The operation of the rotation drive motor 13 is controlled by a dedicated control unit.

The detector unit 11 is disposed at a position facing the X-ray generation unit 10, and connected to the main body 15 through the second arm 20. As described above, the second arm 14 is rotated by the rotation drive motor 13 and vertically moved by the vertical drive motor 16.

Hereinafter, the second arm 20 of the medical diagnostic apparatus according to the embodiment of the present invention will be described in greater detail.

The second arm 20 has a substantial U-shape, one end of which is in connection with the detector unit 11 while the other end is in connection with the elevator unit 12 of the main body 15.

Figure 4:
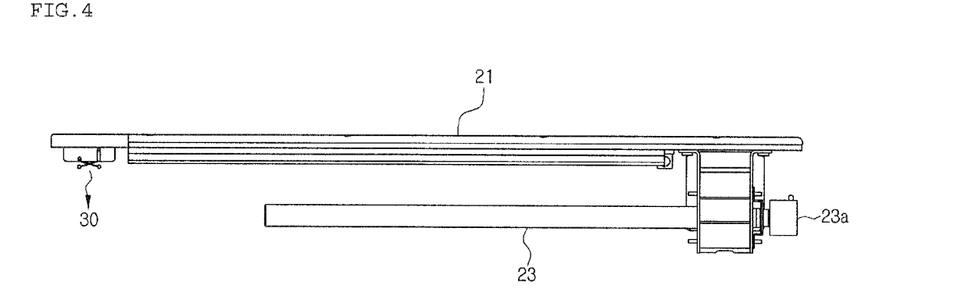
FIG. 4 is a plan view showing a guide rod of a second arm of the medical diagnostic apparatus according to the embodiment of the present invention.
Figure 5:
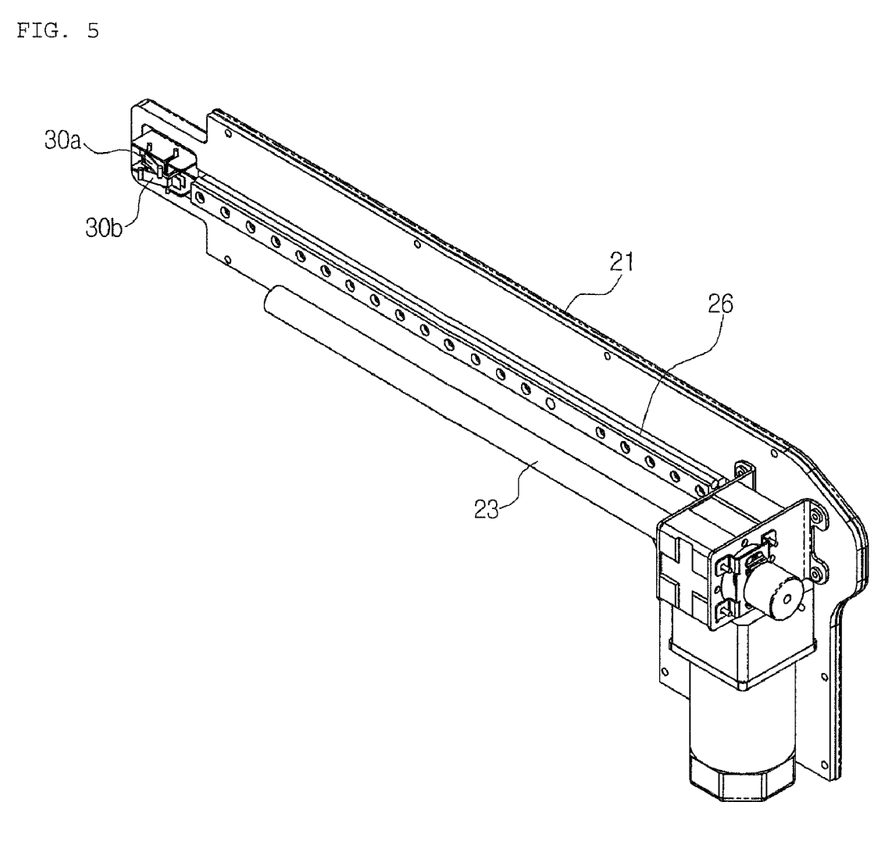
FIG. 5 is a perspective view showing a guide rod of the second arm of the medical diagnostic apparatus according to the embodiment of the present invention.
Figure 6:
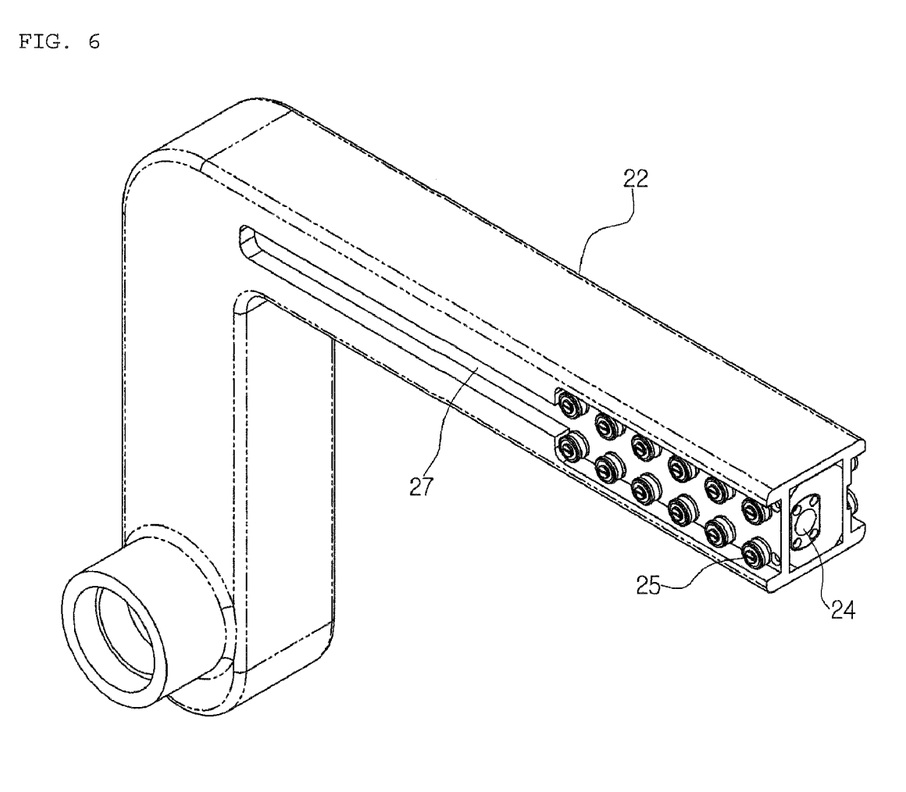
FIG. 6 is a view showing rollers of the second arm of the medical diagnostic apparatus according to the embodiment of the present invention.
Figure 7:
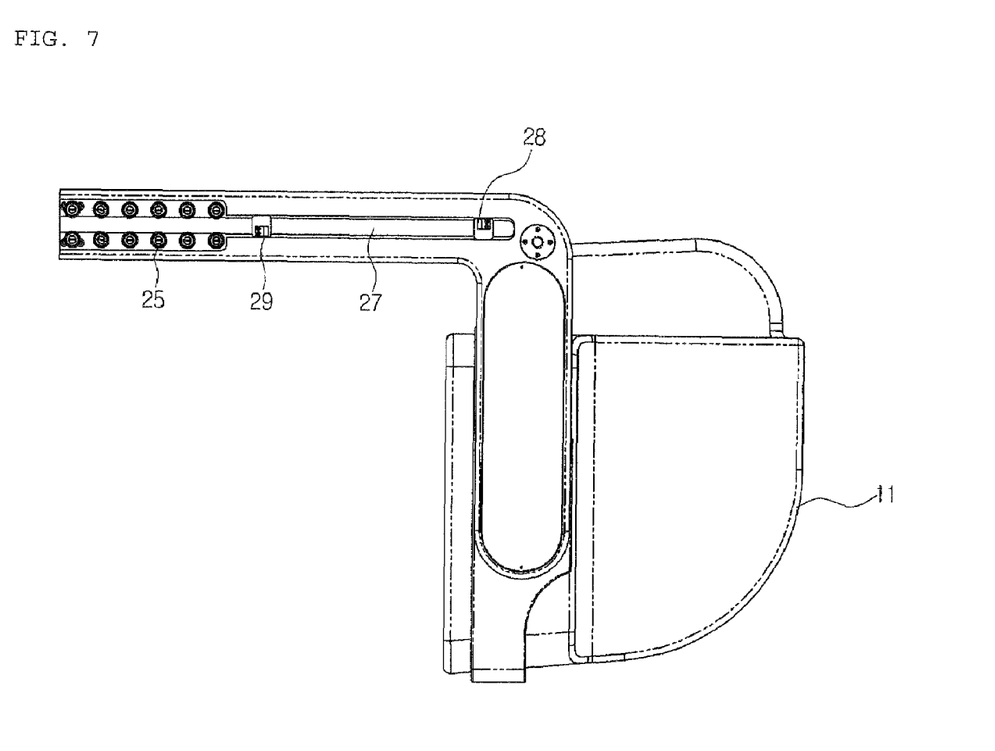
FIG. 7 is a view showing stoppers of the second arm of the medical diagnostic apparatus according to the embodiment of the present invention.

As shown in FIG. 4 through to FIG. 7, the second arm 20 comprises a guide groove unit 22 connected to the detector unit 11 and a guide rod unit connected to the elevator unit 12 of the main body 15. The guide rod unit comprises a guide rod 23, a guide rod drive motor 23a, upper and lower covers, and a second guide plate 21.

The guide groove unit 22 comprises a guide rod hole 24 formed at about the center thereof, a plurality of second rollers 25 mounted to depressed parts formed on both sides of the guide groove unit 22, and a guide rail groove 27. A screw thread is formed on a surface of the guide rod hole 24. The guide rail groove 27 is disposed between the depressed part, where the second rollers 25 are mounted, and the detector unit 11.

The guide rod 23 including a screw thread on a surface thereof is connected with the elevator unit 12 and rotated by the guide rod drive motor 23a. The guide rod 23 is inserted in the guide rod hole 24 formed at the guide groove unit 22. As the screw thread on the surface of the guide rod 23 is engaged with the screw thread of the guide rod hole 24, the guide rod 23 is rotated by the guide rod drive motor 23a and consequently, the guide groove unit 22 is moved forward and backward by the screw connection.

Inside the second guide plate 21 formed on both sides of the guide rod 23, the guide rail 26 is mounted in a length direction of the second guide plate 21. The guide rail 26 is slid according to the forward and backward movement of the guide groove unit 22 in contact with the plurality of rollers 25 formed on both sides of the guide groove unit 22. By this operation, damage of the guide rod 23 by load of the second arm 20 can be prevented, while promoting a smoother forward and backward operation of the guide groove unit 22. In addition, the guide rail 26 passed through in contact with the rollers 25 is fitted in the guide rail groove 27 formed at a rear part of the rollers 25.

As shown in FIG. 4 and FIG. 5, a limit switch 30 is provided at one end of the second guide plate 21. The limit switch 30 comprising a pair of switches, that is, an upper and lower limit switches 30a and 30b, defines maximum and minimum limits of the forward and backward operation of the guide groove unit 22 in contact with a stopper that will be described later.

Also, as shown in FIG. 7, the guide groove unit 22 comprises a pair of stoppers 28 and 29 formed at the guide rail groove 27 disposed at one side thereof. More specifically, the first stopper 28 is disposed at an upper part of the one end of the guide rail groove 27, adjacent to the detector unit 11, and is brought into contact with the upper limit switch 30a of the pair of limit switches in accordance with the forward and backward movement of the guide groove unit 22, thereby stopping the forward and backward movement of the guide groove unit 22 and thus defining the minimum length of the second arm 20.

The second stopper 29 is disposed at a lower part of the other end of the guide rail groove 27, adjacent to the rollers 25, and is brought into contact with the lower limit switch 30b of the pair of limit switches in accordance with the forward and backward movement of the guide groove unit 22, thereby stopping the movement of the guide groove unit 22 and thus defining the maximum length of the second arm 20.

As described above, a movable distance range of the second arm 20 can be established by the limit switch 30 and the stoppers 28 and 29. Therefore, the second arm 20 can be moved stably, not being damaged nor causing an operational error due to an excessive operation load thereof.

In addition, since the second arm 20 can be moved forward and backward by a combined operation between the guide groove unit 22 and the guide rod 23, a distance from the main body 15 to a surface of the detector unit 11 can be adjustable, for example, from at least 534 mm to at most 884 mm.

Furthermore, since the length of the second arm 20 is adjustable, the maximum SID required for the horizontal photographing keeping the patient in a standing position can be secured although the first arm 14 is shortened than in a conventional diagnostic apparatus. Moreover, as well as securing the maximum SID required for the vertical photographing keeping the patient in a lying position, the medical diagnostic apparatus according to the embodiment of the present invention can be easily installed in buildings with a general floor height.

According to the embodiment of the present invention, since the second arm 20, replacing a C-shape arm of the conventional diagnostic apparatus, can perform the forward and backward movement by the combined operation between the guide groove unit 22 and the guide rod 23, the length of the second arm 20 is adjustable. Accordingly, the maximum SID required for both the horizontal and the vertical photographing can be guaranteed even with the first arm 14 set shorter than in the conventional art. In addition, installation of the medical diagnostic apparatus in a general building is facilitated.

In comparison with the conventional art, a length of a main body 15 can be reduced while increasing the maximum movable distance of the elevator unit 12. Also, the length of the arms 14 and 20 connected to the main body 15 and an X-ray generation unit 10 can be highly reduced while securing the required maximum SID.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A medical diagnostic apparatus comprising an X-ray generation unit (10), a first arm (14) moving the X-ray generation unit (10) forward and backward, a detector (11) facing the X-ray generation unit (10) and receiving an X-ray emitted from the X-ray generation unit (10), a second arm (20) connected to the detector unit (11), and a main body (15) including an elevator unit (12) connected with one end of each the first arm (14) and the second arm (20), a vertical drive motor (16) moving the elevator unit (12), a rotation drive motor (13) rotating the elevator unit (12), and an elevation rail mounted for the elevator unit (12) to move vertically therealong, wherein the second arm (20) comprises:
a guide rod (23) connected to the main body (15);
a drive motor (23*a*) rotating the guide rod (23); and
a guide groove unit (22) including a guide rod hole (24) formed with a screw thread for screw-fitting with the guide rod (23) to insert therein the guide rod (23);

wherein the second arm (20) further comprises a second guide plate (21) disposed on both sides of the guide rod (23), and a guide rail (26) additionally formed on an inside of the second guide plate (21), and the guide groove unit (22) further comprises a plurality of rollers (25) formed on both sides thereof to contact with the guide rail (26), and a guide rail groove (27) formed also on both sides thereof to insert the guide rail (26) therein.

2. The medical diagnostic apparatus according to claim 1, wherein the second arm (20) further comprises a pair of limit switches (30*a*, 30*b*) respectively formed on upper and lower parts of one end of the second guide plate (21), and the guide groove unit (22) further comprises a first stopper (28) formed at an upper part of the one end of the guide rail groove (27) and brought into contact with the upper limit switch (30*a*) of the pair of limit switches, and a second stopper (29) formed at a lower part of the other end of the guide rail groove (27) and brought into contact with the lower limit switch (30*b*) of the pair of limit switches.

* * * * *